(12) United States Patent
Fung (10) Patent No.: US 12,083,265 B2
(45) Date of Patent: Sep. 10, 2024

(54) VAPORIZER APPARATUS AND METHOD EMPLOYING MULTIPLE VAPORIZER CARTRIDGES

(71) Applicant: Daniel Y. Fung, New York, NY (US)

(72) Inventor: Daniel Y. Fung, New York, NY (US)

(73) Assignee: Daniel Y. Fung, New York, NY (US)

( * ) Notice: Subject to any disclaimer, the term of this patent is extended or adjusted under 35 U.S.C. 154(b) by 903 days.

(21) Appl. No.: 17/254,796

(22) PCT Filed: Jun. 20, 2019

(86) PCT No.: PCT/US2019/038165
§ 371 (c)(1),
(2) Date: Dec. 21, 2020

(87) PCT Pub. No.: WO2020/005695
PCT Pub. Date: Jan. 2, 2020

(65) Prior Publication Data
US 2021/0260307 A1    Aug. 26, 2021

Related U.S. Application Data

(60) Provisional application No. 62/689,648, filed on Jun. 25, 2018.

(51) Int. Cl.
*A61M 15/00* (2006.01)
*A24F 40/30* (2020.01)
(Continued)

(52) U.S. Cl.
CPC .......... *A61M 15/0003* (2014.02); *A24F 40/30* (2020.01); *A24F 40/42* (2020.01);
(Continued)

(58) Field of Classification Search
CPC .......... A61M 15/0003; A61M 15/0021; A61M 15/06; A61M 11/042; A61M 2205/505;
(Continued)

(56) References Cited

U.S. PATENT DOCUMENTS 2,418,141 A  *  4/1947  Salazar ................. H01M 10/46
                                                      429/100
9,936,737 B2     4/2018  Cameron et al.
(Continued)

FOREIGN PATENT DOCUMENTS

CN    203538384 U    4/2014
KR    20130001035 U  2/2013

OTHER PUBLICATIONS

EP Search Report Ser. No. 198261273 dated Feb. 17, 2022 (Feb. 17, 2022).

(Continued)

*Primary Examiner* — Bradley H Philips
*Assistant Examiner* — Savannah L Gabriel
(74) *Attorney, Agent, or Firm* — Carlos R. Villamar; The Villamar Firm PLLC (57) ABSTRACT

A vaporizer device and method of using same and employing multiple vaporizer cartridges, including a single vaporizer housing having a plurality of vaporizer cartridge openings and a plurality of battery device openings; a plurality of vaporizer cartridges removably disposed within the plurality of vaporizer cartridge openings; a plurality of vaporizer batteries removably disposed within the plurality of vaporizer cartridge openings and respectively coupled to the plurality of vaporizer cartridges to supply power thereto to vaporizer respective product in the respective vaporizer cartridges; and a plurality of vaporizer mouth pieces removably coupled to the plurality of vaporizer cartridges to receive the respective vaporized product from the respective vaporizer cartridges.

13 Claims, 6 Drawing Sheets

(51) Int. Cl.
*A24F 40/42* (2020.01)
*A24F 40/65* (2020.01)
*A61M 15/06* (2006.01)

(52) U.S. Cl.
CPC ......... *A24F 40/65* (2020.01); *A61M 15/0021* (2014.02); *A61M 15/06* (2013.01); *A61M 2205/3584* (2013.01); *A61M 2205/8212* (2013.01)

(58) Field of Classification Search
CPC .. A61M 2205/8237; A61M 2205/3569; A61M 15/00; A61M 15/0001; A61M 15/0025; A61M 15/0065; A61M 15/0086; A61M 2205/8206; A24F 40/30; A24F 40/42; A24F 40/65; A24F 40/90; A24F 40/95
See application file for complete search history.

(56) References Cited

U.S. PATENT DOCUMENTS

| | | | | |
|---|---|---|---|---|
| 10,136,679 | B1* | 11/2018 | Shotey | H05B 1/0227 |
| 2002/0129812 | A1* | 9/2002 | Litherland | B05B 17/0646 |
| | | | | 128/200.14 |
| 2014/0261488 | A1 | 9/2014 | Tucker | |
| 2015/0053217 | A1 | 2/2015 | Steingraber et al. | |
| 2015/0257447 | A1* | 9/2015 | Sullivan | A61M 15/06 |
| | | | | 131/329 |
| 2016/0206001 | A1* | 7/2016 | Eng | A24F 40/30 |
| 2016/0331035 | A1 | 11/2016 | Cameron | |
| 2016/0353800 | A1* | 12/2016 | Di Carlo | A24F 40/30 |
| 2017/0135408 | A1 | 5/2017 | Cameron | |
| 2017/0258138 | A1 | 9/2017 | Rostami et al. | |
| 2017/0304563 | A1 | 10/2017 | Adelson | |
| 2017/0354180 | A1* | 12/2017 | Fornarelli | H05B 3/04 |
| 2018/0013104 | A1* | 1/2018 | Qiu | A24F 40/40 |
| 2018/0084828 | A1* | 3/2018 | Phillips | H05B 1/0244 |
| 2018/0263286 | A1* | 9/2018 | Reevell | A24F 40/40 |
| 2018/0289069 | A1* | 10/2018 | Reevell | A24F 40/50 |
| 2020/0170295 | A1* | 6/2020 | Grimm | A24F 13/00 |
| 2020/0275693 | A1 | 9/2020 | Bowen et al. | |

OTHER PUBLICATIONS

PCT ISR and WO Ser. No. PCT/US2019/038165 dated Sep. 11, 2019 (Sep. 11, 2019).

160019-001 CA Office Action Application No. 3,104,636; Apr. 11, 2024 (Apr. 11, 2024).

* cited by examiner

VAPORIZER APPARATUS AND METHOD EMPLOYING MULTIPLE VAPORIZER CARTRIDGES

BACKGROUND OF THE INVENTION

Cross Reference to Related Documents

The present invention is a PCT Patent application claiming priority to U.S. Provisional Patent Application Ser. No. 62/689,648 DANIEL Y. FUNG, entitled "VAPORIZER APPARATUS AND METHOD EMPLOYING MULTIPLE VAPORIZER CARTRIDGES," filed on 25 Jun. 2018, the entire disclosure of which is hereby incorporated by reference herein.

FIELD OF THE INVENTION

The present invention generally relates to vaporizer devices, and more particularly to a vaporizer apparatus and method employing multiple vaporizer cartridges, and the like.

DISCUSSION OF THE BACKGROUND

In recent years, vaporizer devices for vaporing various products have been developed. However, such devices typically are lacking in effective method for switching between products, and the like, in an efficient and cost-effective manner.

SUMMARY OF THE INVENTION

Therefore, there is a need for an apparatus and method that addresses the above and other problems. The above and other problems are addressed by the illustrative embodiments of the present invention, which provide a vaporizer apparatus and method employing multiple vaporizer cartridges, and the like. The illustrative apparatus and method can include one or more power source coupled ergonomically into a single vaporizer device configured to accept two or more vaporizer cartridges, simultaneously. For the purposes of this description, an illustration using two vaporizer cartridges with two conjoined independent power sources is described to address the above and other problems. Advantageously, twice as much volume of vapor for can be produced from a same single draw, for example, allowing two sub-par simultaneous vaporizer draws to average out to a single impressive vaporizer experience. In addition, as a user notices a diminishing vaporizer experience, for example, because one or more of the vaporizer cartridge is empty, one or more of the cartridge can be replaced with a fresh cartridge. Further, a user can simultaneously vaporize from two vaporizer cartridges at the same time, with the added ability to mix and match different styles and/or strains of vaporizer oils, products, and the like, to further customize a medicinal or other vaporizer experience, as compared to conventional vaporizer devices having a single vaporizer cartridge per vaporizer battery, and the like.

Accordingly, in illustrative aspects of the present invention there is provided a vaporizer device and method of using same and employing multiple vaporizer cartridges, including a single vaporizer housing having a plurality of vaporizer cartridge openings and a plurality of battery device openings; a plurality of vaporizer cartridges removably disposed within the plurality of vaporizer cartridge openings; a plurality of vaporizer batteries removably disposed within the plurality of vaporizer cartridge openings and respectively coupled to the plurality of vaporizer cartridges to supply power thereto to vaporizer respective product in the respective vaporizer cartridges; and a plurality of vaporizer mouth pieces removably coupled to the plurality of vaporizer cartridges to receive the respective vaporized product from the respective vaporizer cartridges.

In the vaporizer device and method, the plurality of vaporizer batteries include a single battery device.

The vaporizer device and method further includes a single mouth piece covering the plurality of vaporizer mouth pieces.

The vaporizer device and method further includes a single fire button configured to allow voltage to pass voltage from the vaporizer batteries to the vaporizer cartridges.

The vaporizer device and method further includes a respective plurality of fire buttons configured to respectively allow voltage to pass voltage from the respective vaporizer batteries to the respective vaporizer cartridges.

The vaporizer device and method further includes a plurality of voltage adjustment controls for the respective batteries and configured to throttle how much voltage is passed to the respective vaporizer cartridges allowing for adjustment of an amount of respective vapor delivered by the respective vaporizer cartridges.

The vaporizer device and method further includes a Bluetooth smartphone application configured to control the voltage adjustment controls.

In the vaporizer device and method, the single vaporizer housing comprises a respective plurality of vaporizer housings attached together and each having a vaporizer cartridge opening and a battery device opening.

In the vaporizer device and method, the single vaporizer housing includes a slider assembly configured to accept the plurality of vaporizer batteries having different vertical heights.

Still other aspects, features, and advantages of the present invention are readily apparent from the following detailed description, by illustrating a number of illustrative embodiments and implementations, including the best mode contemplated for carrying out the present invention. The present invention is also capable of other and different embodiments, and its several details can be modified in various respects, all without departing from the spirit and scope of the present invention. Accordingly, the drawings and descriptions are to be regarded as illustrative in nature, and not as restrictive.

BRIEF DESCRIPTION OF THE DRAWINGS

The embodiments of the present invention are illustrated by way of example, and not by way of limitation, in the figures of the accompanying drawings and in which like reference numerals refer to similar elements and in which.

DETAILED DESCRIPTION OF THE PREFERRED EMBODIMENTS

Figure 1:
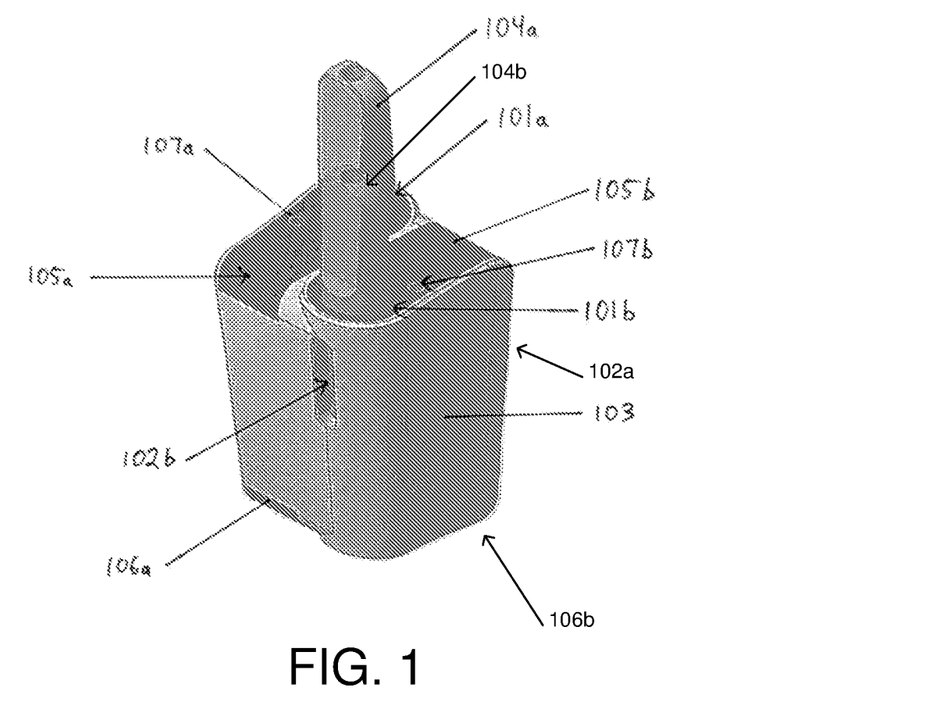
FIG. 1 shows an illustrative top side view of an auto-draw, concealer type, double vaporizer cartridge device.

Referring now to the drawings, wherein like reference numerals designate identical or corresponding parts throughout the several views, and more particularly to FIG. 1 thereof, there is illustrated a top side view of an auto-draw, concealer type, double vaporizer cartridge device, according to an illustrative embodiment. In FIG. 1, first and second cartridge barrel openings 101a and 101b, including respective vaporizer cartridges 104a and 104b inserted therein, and ready to operate in such configuration. Sight view windows 102a and 102b reveal a remaining amount of vaporizer product, such as vaporizer oil level, and the like, in respective first and second cartridge that are loaded into the first and second cartridge barrel openings 101a and 101b. A conjoined double battery body housing 103 is configured to maintain separate sides of the vaporizer device, advantageously, providing independent, respective battery power sources. Top side battery covers 105a and 105b are configured cover and protect component parts of the vaporizer device. The top side battery covers 105a and 105b are secured in place, for example, using 1/16" Hex Screws 107a and 107b. Bottom side battery covers 106a and 106b cover and protect operating parts of the vaporizer device from the bottom side.

In further embodiments, a single battery power source can be employed to operate cartridges in both cartridge barrel openings 101a and 101b. However, it is advantageous to maintain two separate and independent battery power supplies for each respective cartridge in the barrel opening 101a and 101b. For example, if the battery on one side is used up before the other side, the vaporizer device can still operate on the single side. Additionally, the independent batteries re-charge twice as fast with two cables feeding them, whereas if limited to just a single USB micro female recharge port, it would take twice as long to recharge a single battery cell with double the power capacity.

Figure 2:
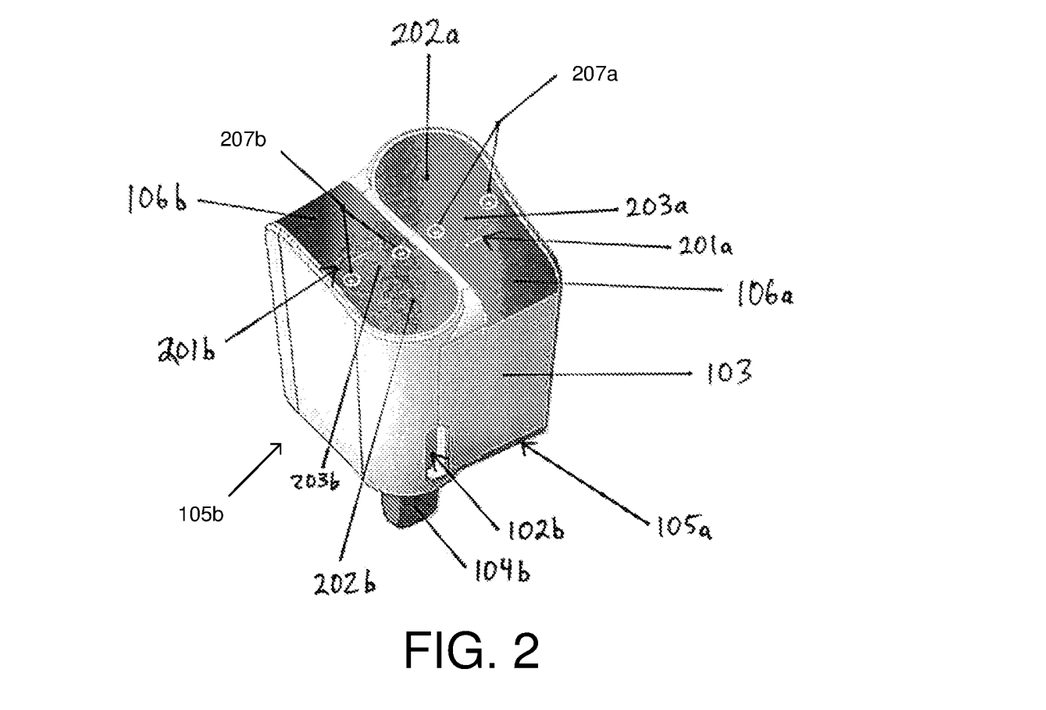
FIG. 2 shows an illustrative bottom side view of the auto-draw, concealer type, double vaporizer cartridge device of FIG. 1.

FIG. 2 shows an illustrative bottom side view of the auto-draw, concealer type, double vaporizer cartridge device of FIG. 1. In FIG. 2, independent USB micro female charging ports 201a and 201b are provided to recharge respective battery cells for the vaporizer device. The bottom side battery covers 106a and 106b are secured in place using 1/16" Hex Screws 207a and 207b respectively. From this viewpoint the top side battery cover 105a can be seen. Air flow vent holes 202a and 202b allow for inflowing air to be drawn through the vaporizer device. LED 203a and 203b, for example, light up RED while the device is recharging the batteries, and shut off indicating that the batteries are fully recharged.

Figure 3:
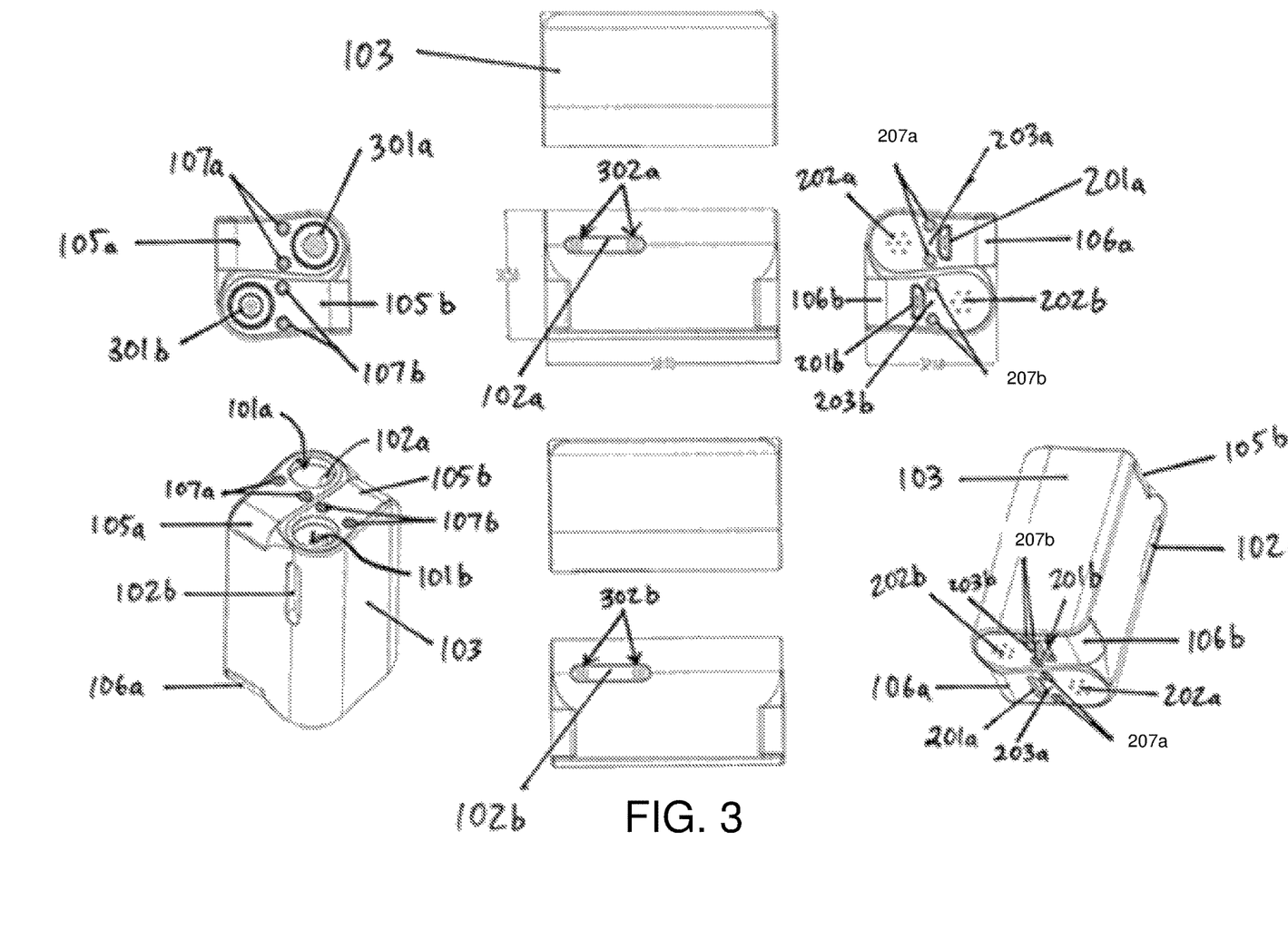
FIG. 3 shows an illustrative 3-D CAD rendering with various views of the auto-draw, concealer type, double vaporizer cartridge device of FIGS. 1-2.

FIG. 3 shows an illustrative 3-D CAD rendering with various views of the auto-draw, concealer type, double vaporizer cartridge device of FIGS. 1-2. In FIG. 3, the vaporizer cartridge barrels 101a and 101b, along with the vaporizer oil sight view windows 102a and 102b, align with USB micro female charging ports 201a and 201b, respectively. At the bases of vaporizer cartridge barrels 101a and 10b reside magnetic posts and suction draw sensors 301a and 301b that attach to the vaporizer cartridges using magnetic 510 thread adapters 405a and 405b (shown in FIG. 4) that are threaded onto the bases of universal 510 thread vaporizer cartridges 104a and 104b. With such magnetic thread adapters 405a and 405b, advantageously, the user can pull (e.g., yank) on the cartridges 104a and 104b (e.g., as shown in FIGS. 1-2) to disconnect the cartridges from the vaporizer device and switch them out with new vaporizer oil cartridges, and the like, with which to mix-and-match a vaporizer experience with different combination pairs of cartridges. The magnetic thread adapters 405a and 405b can be modified, advantageously, to adapt to future threading standards. The conjoined double battery body housing 103 with sight views 102a and 102b can reveal the remaining vaporizer oil level in each respective side of the device to the user. The air intake vents 202a and 202b allow air to flow thru the device for the draw activation of the batteries.

In this embodiment, there are no fire buttons to operate the independent battery power sources, as the power is activated using the suction sensors 301a and 301b. When the user draws from the attached vaporizer cartridge(s) 104a and 104b, the suction of their draw activates the magnetic post and suction sensors 301a and 301b at the base of the vaporizer cartridge openings 101a and 101b respectively. When the magnetic post and suction sensors 301a and 301b are activated from sensing the draw suction from the user, the sensors enable a circuit and allowing power from the independent rechargeable batteries 401a and 401b (shown in FIG. 4) to flow to the vaporizer cartridges 104a and 104b. The vapor from the vaporizer cartridges 104a and 104b can be produced for as long as the magnetic post and suction sensors 301a and 301b continue to sense the draw suction from the user drawing and sucking on the vaporizer cartridges 104a and 104b. As soon as the user ceases drawing on the vaporizer cartridges 104a and 104b, the voltage cuts off and the vaporizer cartridges stop producing vapor until the next time the sensors 301a and 301b are activated with the next draw from the user. When the magnetic post and suction sensor 301a and 301b are in their activated state, in addition to the voltage being allowed to flow to power the vaporizer cartridges 104a and 104b, LEDs 302a and 302b can light up GREEN for as long as the circuits are enabled, and the LEDs 302a and 302b can shut off when the circuits are off. Additionally, CPU chips 402a and 402b and circuit board 403a and 403b (shown in FIG. 4) operate each independent batteries 401a and 401b, and are designed to include a 10-second safety cut off, and the like, which disables the vaporizer circuits, automatically, after they have been activated for 10 seconds, and the like. Such safety feature prevents overheating of the batteries of the vaporizer devices. The LEDs 203a and 203b located on the bottom side battery covers 106a and 106b, respectively, light up RED to indicate that the independent batteries are recharging, and the LEDs shut off when the batteries are fully recharged. The CPU chips 402a and 402b and the circuit boards 403a and 403b (shown in FIG. 4) operate each independent batteries 401a and 401b, and also include overcharge safety features designed into the boards 403a and 403b that prevent the batteries from getting overcharged when being recharged. The CPU chips 402a and 402b and the circuit boards 403a and 403b that operate each independent battery 401a and 401b, also are designed to regulate the voltage, so that the current is consistent when being sent to power the vaporizer cartridges 104a and 104b (e.g., as shown in FIGS. 1, 2, 4, 5 and 6)

Figure 4:
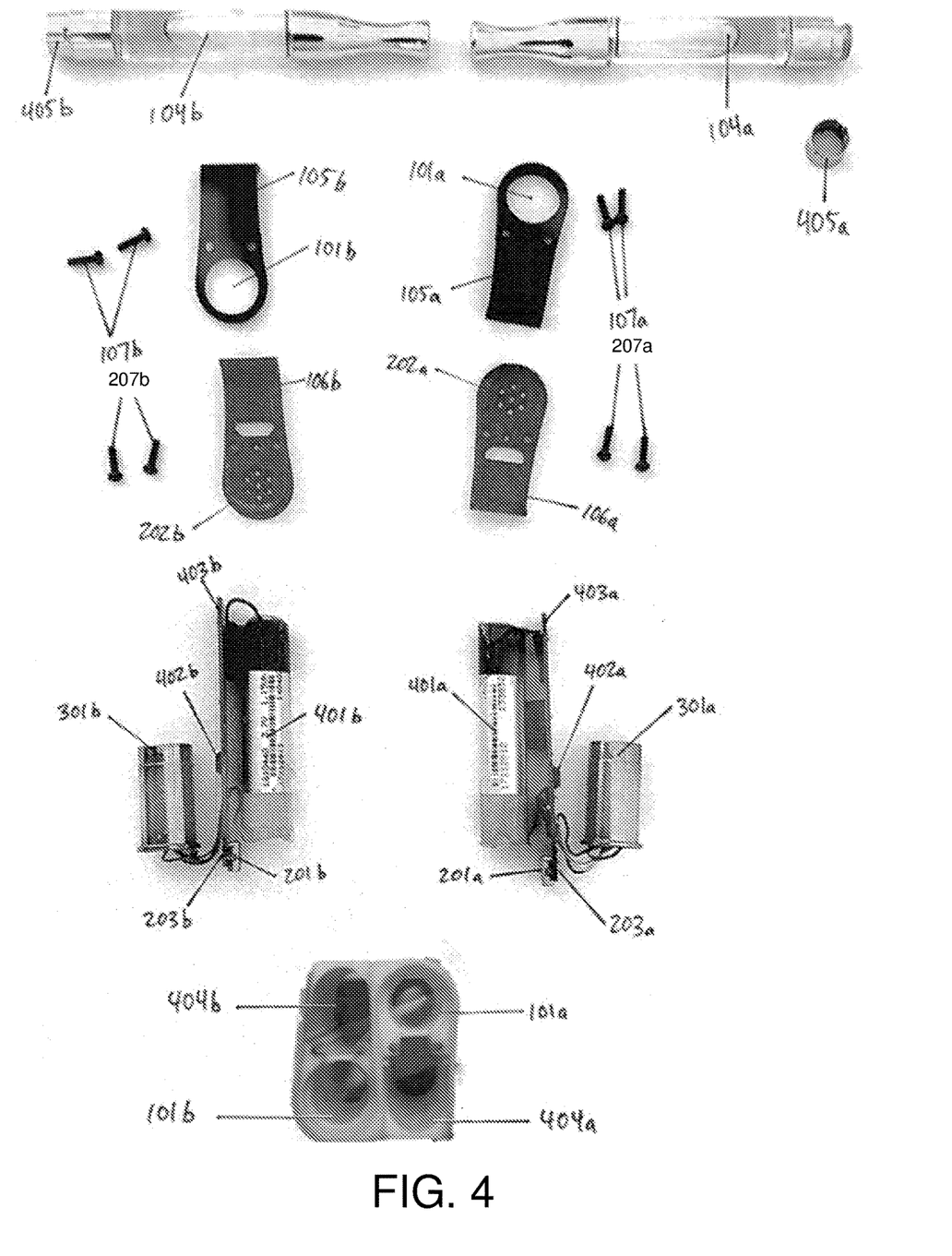
FIG. 4 shows an illustrative exploded view of the auto-draw, concealer type, double vaporizer cartridge device of FIGS. 1-3.

FIG. 4 shows an illustrative exploded view of the auto-draw, concealer type, double vaporizer cartridge device of FIGS. 1-3. The CPU chips 402a and 402b and the circuit boards 403a and 403b control when the vaporizer device fires, regulates the current, and manages the safety features for the rechargeable battery cells 401a and 401b to prevent overheating and overcharging. The CPU chips 402a and 402b and circuit boards 403a and 403b are inserted inside the double battery body 103, in openings 404a and 404b respectively, when fully assembled. Similarly, the magnetic post and suction sensors 301a and 301b are installed at the base of vaporizer cartridge openings 101a and 101b respectively, when fully assembled. The top side battery covers 105a and 105b and the bottom side battery covers 106a and 106b are secured in place, for example, using respective hex screws 107a and 107b and 207a and 207b when fully assembled. The vaporizer cartridges 104a and 104b are shown with corresponding 510 thread magnetic coupling adapters 405 and 405b, which are used to connect the vaporizer cartridges 104a and 104b to the magnetic draw and suction sensors 301a and 301b, respectively.

Advantageously, the present invention improves the consumer experience of inhaling vaporizer cartridges by creating a power source system that allows the user to vaporize simultaneously more than one vaporizer cartridge, and more particularly to a method and system for mixing and matching vaping different formulations and strains of vaporizer oil.

In the illustrative embodiments, two or more vaporizer cartridges and respective independent vaporizer batteries disposed within a single body unit can be employed, based on the teachings of the present invention, as will be appreciated by those of ordinary skill in the relevant art(s). Advantageously, such configuration provides the ability for a user to mix-and-match different vaporizer cartridges into a combined vaporizer experience, where the vapors blend in the mouth of the user as the user inhales.

Figure 5:
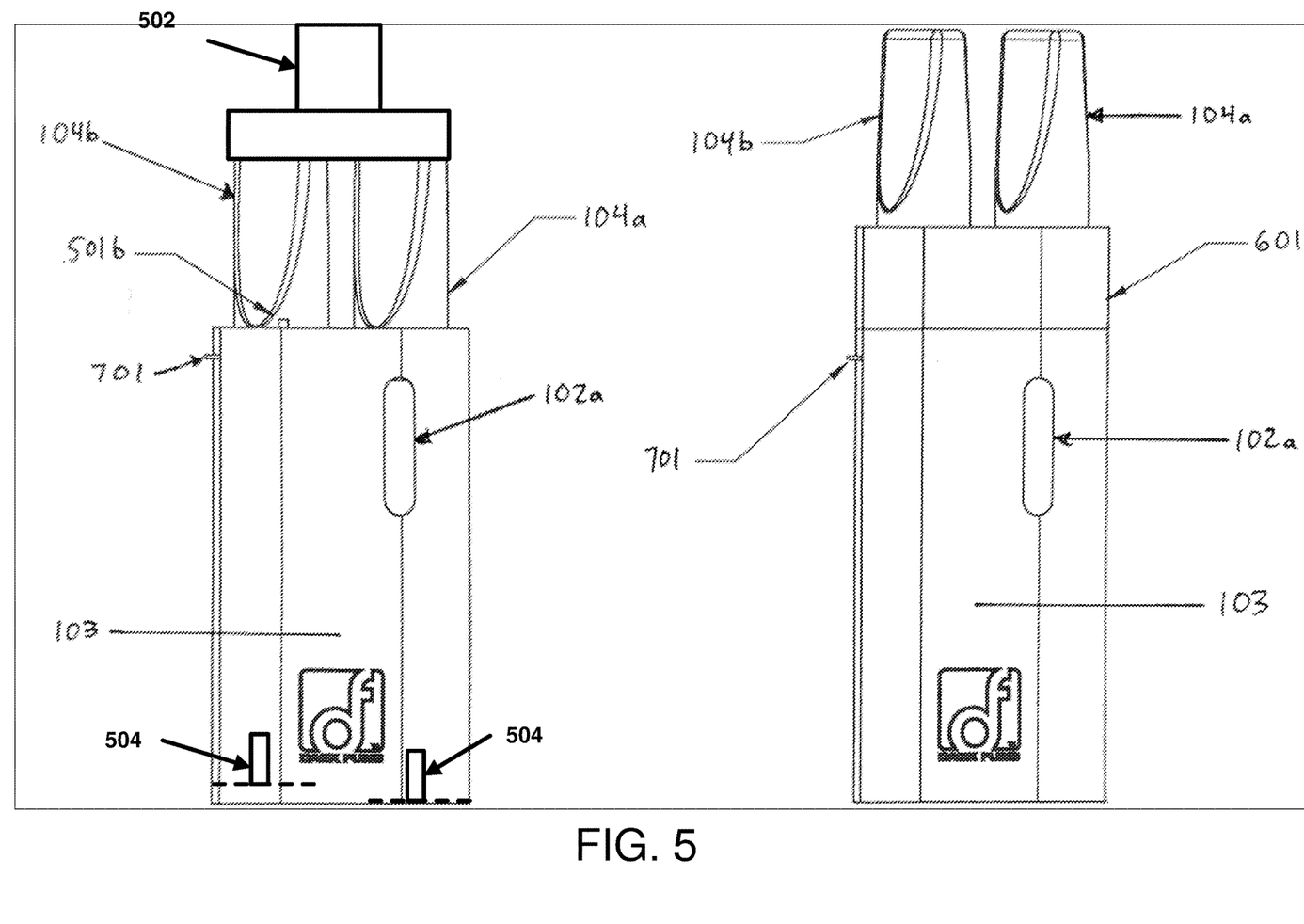
FIG. 5 shows an illustrative front side view of an auto-draw, concealer type, double vaporizer cartridge device, with additional depictions of voltage adjustment controls, a riser, and a keychain ring.

In the illustrative embodiments, a single mouthpiece 502 shown in FIG. 5 that covers the mouthpieces of the two cartridges 104a and 104b of FIG. 5 to create a single, wider mouthpiece 502 to draw from can be employed, based on the teachings of the present invention, as will be appreciated by those of ordinary skill in the relevant art(s). For example, a single wider mouthpiece 502 can be configured to cover the vaporizer cartridges 104a and 104b, advantageously, allowing user to not have to draw on two separate mouthpieces simultaneously.

In the illustrative embodiments, a single firing button can be employed so as to fire the vaporizer cartridges simultaneously, based on the teachings of the present invention, as will be appreciated by those of ordinary skill in the relevant art(s). For example, a single fire button can be employed instead of using the magnetic draw and suction sensors 301a and 301b to detect the users draw and inhale to close the circuit and pass the voltage from the battery cells 401a and 401b to the vaporizer cartridges 104a and 104b, wherein magnetic post(s) can be employed, instead of sensors 301a and 301b to couple and affix the vaporizer cartridges 104a and 104b to the device.

In the illustrative embodiments, multiple firing buttons can be employed to control each vaporizer cartridge by respective button fire independently, based on the teachings of the present invention, as will be appreciated by those of ordinary skill in the relevant art(s). For example, two fire buttons can be employed in the device to control firing of the vaporizer cartridges 104a and 104b independently by pressing the respective fire button dedicated to each side of the device. In this configuration, both fire buttons can be employed instead of using the magnetic draw and suction sensors 301a and 301b to detect the users draw and inhale to close the circuit and pass the voltage from the battery cells 401a and 401b to the vaporizer cartridges 104a and 104b, wherein magnetic post(s) can be employed, instead of sensors 301a and 301b to couple and affix the vaporizer cartridges 104a and 104b to the device.

In the illustrative embodiments, a single charging port can be employed to recharge both batteries in the device, based on the teachings of the present invention, as will be appreciated by those of ordinary skill in the relevant art(s).

In the illustrative embodiments, a single relatively large battery that is capable to fire multiple vaporizer cartridges simultaneously can be employed, as will be appreciated by those of ordinary skill in the relevant art(s). For example, a single battery cell 401 with a larger capacity can be employed to power both vaporizer cartridge openings 101a and 101b.

In the illustrative embodiments, separate individual batteries with magnetic sides configured on the bodies thereof to allow pulling the batteries apart and mixing and matching the batteries to allow to allow swapping out for freshly charged batteries without waiting out the battery recharge time can be employed, based on the teachings of the present invention, as will be appreciated by those of ordinary skill in the relevant art(s).

In the illustrative embodiments, three or more vaporizer batteries being conjoined in order to vaporizer three or more vaporizer cartridges, simultaneously or in series can be employed, based on the teachings of the present invention, as will be appreciated by those of ordinary skill in the relevant art(s).

In the illustrative embodiments, a magnetic threading adapter can be configured with 510 type threads, advantageously, with the magnetic threading adapters modified to adapt to any suitable future threading standard, so that adapter change is simple and cheap, providing flexibility for future standards, avoiding a need for device configuration changes, based on the teachings of the present invention, as will be appreciated by those of ordinary skill in the relevant art(s).

The present invention includes recognition of and solves the problem, for example, that most 0.5 ml vaporizer cartridges differ from 1.0 ml vaporizer cartridges in terms of the overall height of the vaporizer cartridge. For example, when a bigger vaporizer cartridge is employed, the device typically can only be made taller, as wider is a cumbersome way to increase the size capacity of a vaporizer cartridge. Accordingly, in the illustrative embodiments, a slider assembly 504 shown in FIG. 5 attaching two separate vaporizer batteries together with the slider assembly 504 of FIG. 5 configured for one battery to be offset at a different vertical height from the other battery to accommodate for cartridge size differences can be employed, based on the teachings of the present invention, as will be appreciated by those of ordinary skill in the relevant art(s).

In the illustrative embodiments, nanotechnology and scientific advancements in materials science can be employed to attach and re-attach multiple vaporizer batteries together for vaping simultaneously or in series, based on the teachings of the present invention, as will be appreciated by those of ordinary skill in the relevant art(s). For example, two separate vaporizer battery systems can be independent and attached together, instead of within a single conjoined body unit 103, for example, using magnetized bodies, nanotechnology materials that allow them to stick to each other, and the like.

In the illustrative embodiments, a single mouth piece and, for example, Bluetooth software, and the like, controlled solenoid valves can be employed to control the mix of vapor from two or more respective cartridges using a smartphone application, and the like, wherein a slider, and the like, can be configured to set a mix ratio, and attenuate the solenoid valves so as to adjust and create a desired mix of vapors from the cartridges, based on the teachings of the present invention, as will be appreciated by those of ordinary skill in the relevant art(s).

In the illustrative embodiments, two vaporizer cartridges and two vaporizer batteries can be employed in a single body unit, and with voltage adjustment controls for the respective batteries to throttle how much voltage is passed to the vaporizer carts 104a and 104b when a user draw and fires the vaporizer device, based on the teachings of the present invention, as will be appreciated by those of ordinary skill in the relevant art(s). Advantageously, such configuration provides a user with volume type controls to adjust the amount of vapor that each side of the device produces when firing using the magnetic draw and suction sensors 301a and 301b to fire the vaporizer device.

In the illustrative embodiments, a configuration with two or more vaporizer cartridges and two or more vaporizer batteries in a single body unit can be employed, and volume button type, voltage adjustment controls can be added to the respective batteries to throttle how much voltage is passed to the vaporizer cartridges 104a and 104b, when the user draws and fires the vaporizer device, based on the teachings of the present invention, as will be appreciated by those of ordinary skill in the relevant art(s). Advantageously, such volume controls can be used to adjust the amount of vapor that each side produces when firing using the manual fire buttons in either one-button or two-button configurations.

In the illustrative embodiments, the voltage adjustment controls can be controlled, for example, using Bluetooth and a smartphone application, and the like, wherein the circuit boards 403a and 403b include Bluetooth, and the like, communication and control capabilities to interface with the smartphone application, based on the teachings of the present invention, as will be appreciated by those of ordinary skill in the relevant art(s).

In the illustrative embodiments, the voltage adjustment controls can utilize two or more vaporizer cartridges, but with a single battery with employed power capacity, based on the teachings of the present invention, as will be appreciated by those of ordinary skill in the relevant art(s).

FIG. 5 shows an illustrative front side view of an auto-draw, concealer type, double vaporizer cartridge device, with additional depictions of voltage adjustment controls, a riser, and a keychain ring. In FIG. 5, the auto-draw, concealer type, double vaporizer cartridge device includes voltage adjustment control 501a and 501b. Logic can be configured, for example, to provide 3 levels of voltage that the user can cycle between and is built into the CPU chips 402a and 402b on circuit boards 403a and 403b and controlled by clicking voltage adjustment control buttons 501a and 501b, respectively.

The present invention includes recognition of and solves the problem, for example, that most 0.5 ml vaporizer cartridges differ from 1.0 ml vaporizer cartridges in terms of the overall height of the vaporizer cartridge. Accordingly, FIG. 5 illustrates a riser 601 which is designed to magnetically attach to the top side of the battery body housing 103. The additional height afforded by riser 601 is to protect the larger 1.0 ml vaporizer cartridges as they protrude more from the battery body housing 103 that is designed to offer protection to the concealed vape cartridges 104a and 104b respectively.

In the illustrative embodiments, a key chain ring 701 can be utilized to offer a convenient method to attach your battery body housing 103 to your key chain or backpack.

Figure 6:
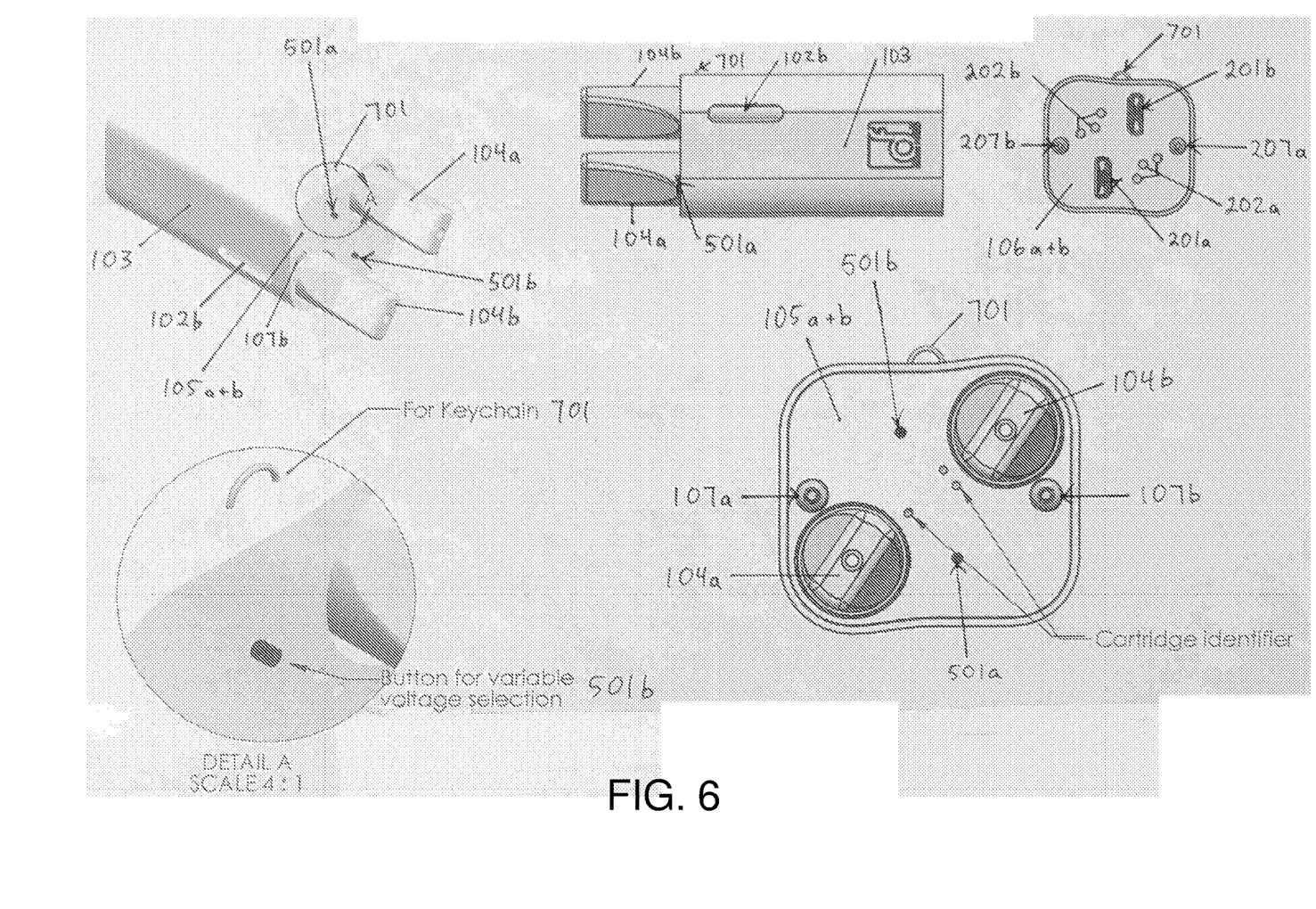
FIG. 6 shows an illustrative top side, bottom side, lying on its side views of the auto-draw, concealer type, double vaporizer cartridge device of FIG. 5.

FIG. 6 shows an illustrative top side, bottom side, lying on its side views of the auto-draw, concealer type, double vaporizer cartridge device of FIG. 5. In FIG. 6, voltage adjustment control buttons 501a and 501b are set into top side battery cover 105a+b (e.g., in this embodiment top side battery cover 105a and 105b are merged into a single piece 105a+b). Merging the top side battery cover into a single piece, advantageously, reduced the number of screws 107a and 107b employed to secure the top, such that a single screw rather than pairs of screws can be employed. The same was done for the bottom side with 207a and 207b being reduced to single screws down from being pairs of screws. The bottom side battery covers have also been merged into a single piece 106a+b like the top side cover. Air flow vents 202a and 202b have holes that are enlarged, and the configuration is modified to allow for more air flow and heat vent release. FIG. 6 includes a 4x scale zoom in of the voltage adjustment control button 501b and key chain ring 701.

Figure 7:
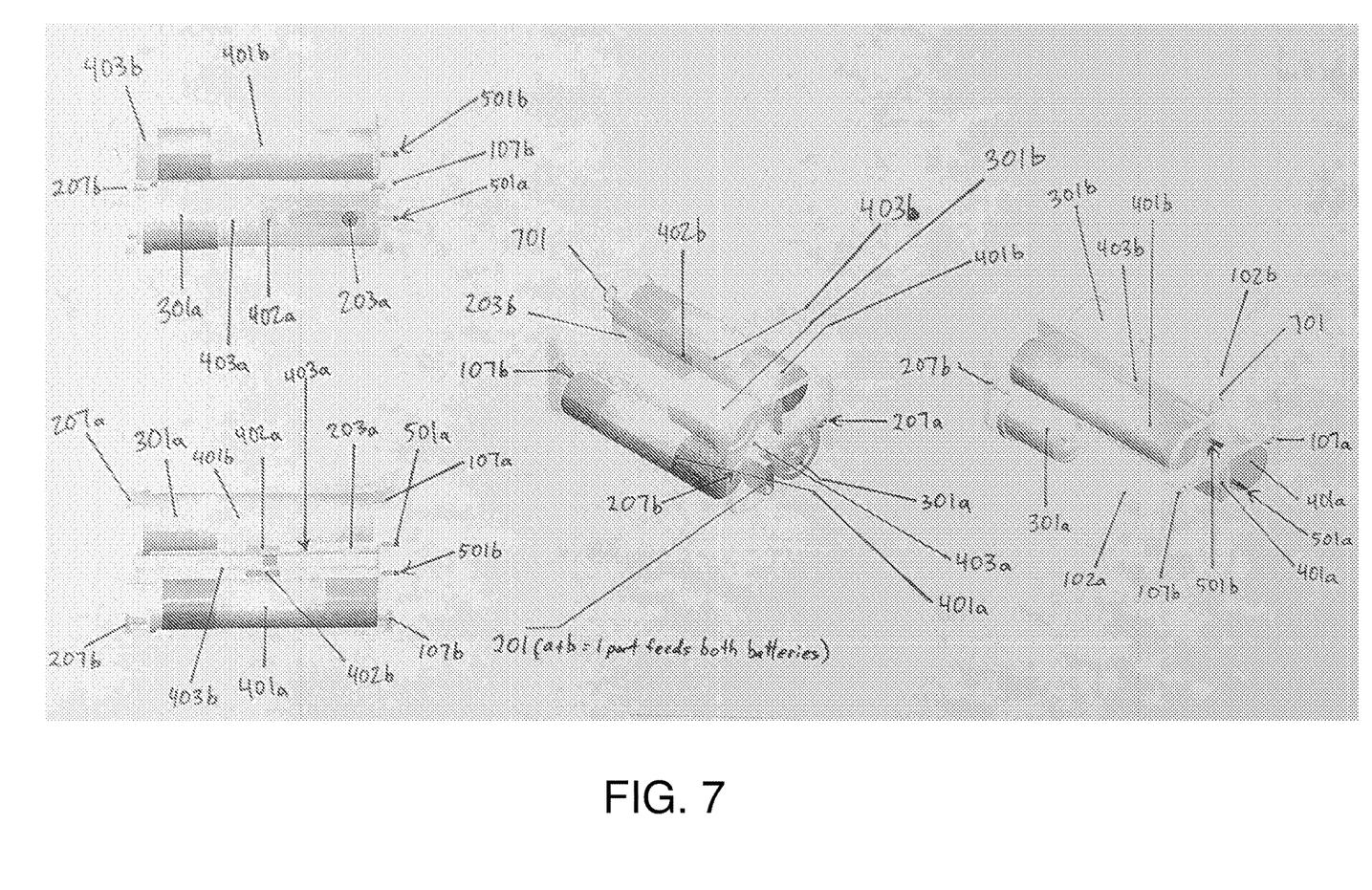
FIG. 7 shows an illustrative transparent view of the auto-draw, concealer type, double vaporizer cartridge device of FIG. 5, with a configuration utilizing only a single port to recharge both batteries of the device.

FIG. 7 shows an illustrative transparent view of the auto-draw, concealer type, double vaporizer cartridge device of FIG. 5, with a configuration utilizing only a single port to recharge both batteries of the device. In FIG. 7, a configuration utilizing only a single port 201a+b to recharge both batteries 401a and 401b of the device is provided. The transparent view illustrates internals of the auto-draw, concealer type, double vaporizer cartridge device. The internals are similar for both FIG. 1 and FIG. 5 embodiments, a difference being that in the FIG. 7 embodiment the independent USB micro female charging ports 201a and 201b have been streamlined to a single USB micro female charging port 201a+b. The logic to manage the recharging of batteries 401a and 401b through a single USB micro female charging port 201a+b is built into the CPU chips 402a and 402b on circuit boards 403a and 403b.

The above-described devices and subsystems of the illustrative embodiments can include, for example, any suitable servers, workstations, PCs, laptop computers, PDAs, Internet appliances, handheld devices, cellular telephones, wireless devices, other devices, and the like, capable of performing the processes of the illustrative embodiments. The devices and subsystems of the illustrative embodiments can communicate with each other using any suitable protocol and can be implemented using one or more programmed computer systems or devices.

One or more interface mechanisms can be used with the illustrative embodiments, including, for example, Internet access, telecommunications in any suitable form (e.g., voice, modem, and the like), wireless communications media, and the like. For example, employed communications networks or links can include one or more wireless communications networks, cellular communications networks, G3 communications networks, Public Switched Telephone Network (PSTNs), Packet Data Networks (PDNs), the Internet, intranets, a combination thereof, and the like.

It is to be understood that the devices and subsystems of the illustrative embodiments are for illustrative purposes, as many variations of the specific hardware used to implement the illustrative embodiments are possible, as will be appreciated by those skilled in the relevant art(s). For example, the functionality of one or more of the devices and subsystems of the illustrative embodiments can be implemented via one or more programmed computer systems or devices.

To implement such variations as well as other variations, a single computer system can be programmed to perform the special purpose functions of one or more of the devices and subsystems of the illustrative embodiments. On the other hand, two or more programmed computer systems or devices can be substituted for any one of the devices and subsystems of the illustrative embodiments. Accordingly, principles and advantages of distributed processing, such as redundancy, replication, and the like, also can be implemented, as desired, to increase the robustness and performance of the devices and subsystems of the illustrative embodiments.

The devices and subsystems of the illustrative embodiments can store information relating to various processes described herein. This information can be stored in one or more memories, such as a hard disk, optical disk, magneto-optical disk, RAM, and the like, of the devices and subsystems of the illustrative embodiments. One or more databases of the devices and subsystems of the illustrative embodiments can store the information used to implement the illustrative embodiments of the present inventions. The databases can be organized using data structures (e.g., records, tables, arrays, fields, graphs, trees, lists, and the like) included in one or more memories or storage devices listed herein. The processes described with respect to the illustrative embodiments can include appropriate data structures for storing data collected and/or generated by the processes of the devices and subsystems of the illustrative embodiments in one or more databases thereof.

All or a portion of the devices and subsystems of the illustrative embodiments can be conveniently implemented using one or more general purpose computer systems, microprocessors, digital signal processors, micro-controllers, and the like, programmed according to the teachings of the illustrative embodiments of the present inventions, as will be appreciated by those skilled in the computer and software arts. Appropriate software can be readily prepared by programmers of ordinary skill based on the teachings of the illustrative embodiments, as will be appreciated by those skilled in the software art. Further, the devices and subsystems of the illustrative embodiments can be implemented on the World Wide Web. In addition, the devices and subsystems of the illustrative embodiments can be implemented by the preparation of application-specific integrated circuits or by interconnecting an appropriate network of conventional component circuits, as will be appreciated by those skilled in the electrical art(s). Thus, the illustrative embodiments are not limited to any specific combination of hardware circuitry and/or software.

Stored on any one or on a combination of computer readable media, the illustrative embodiments of the present inventions can include software for controlling the devices and subsystems of the illustrative embodiments, for driving the devices and subsystems of the illustrative embodiments, for enabling the devices and subsystems of the illustrative embodiments to interact with a human user, and the like. Such software can include, but is not limited to, device drivers, firmware, operating systems, development tools, applications software, and the like. Such computer readable media further can include the computer program product of an embodiment of the present inventions for performing all or a portion (if processing is distributed) of the processing performed in implementing the inventions. Computer code devices of the illustrative embodiments of the present inventions can include any suitable interpretable or executable code mechanism, including but not limited to scripts, interpretable programs, dynamic link libraries (DLLs), Java classes and applets, complete executable programs, Common Object Request Broker Architecture (CORBA) objects, and the like. Moreover, parts of the processing of the illustrative embodiments of the present inventions can be distributed for better performance, reliability, cost, and the like.

As stated above, the devices and subsystems of the illustrative embodiments can include computer readable medium or memories for holding instructions programmed according to the teachings of the present inventions and for holding data structures, tables, records, and/or other data described herein. Computer readable medium can include any suitable medium that participates in providing instructions to a processor for execution. Such a medium can take many forms, including but not limited to, non-volatile media, volatile media, transmission media, and the like. Non-volatile media can include, for example, optical or magnetic disks, magneto-optical disks, and the like. Volatile media can include dynamic memories, and the like. Transmission media can include coaxial cables, copper wire, fiber optics, and the like. Transmission media also can take the form of acoustic, optical, electromagnetic waves, and the like, such as those generated during radio frequency (RF) communications, infrared (IR) data communications, and the like. Common forms of computer-readable media can include, for example, a floppy disk, a flexible disk, hard disk, magnetic tape, any other suitable magnetic medium, a CD-ROM, CDRW, DVD, any other suitable optical medium, punch cards, paper tape, optical mark sheets, any other suitable physical medium with patterns of holes or other optically recognizable indicia, a RAM, a PROM, an EPROM, a FLASH-EPROM, any other suitable memory chip or cartridge, a carrier wave or any other suitable medium from which a computer can read.

While the present inventions have been described in connection with a number of illustrative embodiments, and implementations, the present inventions are not so limited, but rather cover various modifications, and equivalent arrangements, which fall within the purview of the appended claims.

What is claimed is:

1. A vaporizer device employing multiple vaporizer cartridges, the device comprising:
   a single vaporizer housing that is rectangular-shaped and includes top and bottom, front and back, and left and right sides, and having a plurality of vaporizer cartridge openings and a plurality of battery device openings on the top side of the housing;
   a plurality of vaporizer cartridges removably disposed through the top side of the housing within the plurality of vaporizer cartridge openings on the top side of the housing;
   a plurality of vaporizer batteries removably disposed within the plurality of battery device openings and respectively coupled to the plurality of vaporizer cartridges to supply power thereto to vaporize respective product in the respective vaporizer cartridges; and
   a plurality of vaporizer mouth pieces removably coupled to the plurality of vaporizer cartridges to receive the respective vaporized product from the respective vaporizer cartridges.

2. The vaporizer device of claim 1, wherein the plurality of vaporizer batteries comprise a plurality of single battery devices.

3. The vaporizer device of claim 1, further comprising a further mouthpiece configured to cover the plurality of vaporizer mouth pieces.

4. The vaporizer device of claim 1, further comprising a single fire button configured to allow voltage to pass from the vaporizer batteries to the vaporizer cartridges.

5. The vaporizer device of claim 1, further comprising a respective plurality of fire buttons configured to respectively allow voltage to pass from the respective vaporizer batteries to the respective vaporizer cartridges.

6. The vaporizer device of claim 1, further comprising a plurality of voltage adjustment controls for the respective batteries and configured to throttle how much voltage is passed to the respective vaporizer cartridges allowing for adjustment of an amount of respective vapor delivered by the respective vaporizer cartridges.

7. The vaporizer device of claim 6, further comprising a plurality of circuit boards, wherein each of the plurality of circuit boards is associated with a respective voltage adjustment control and is configured to interface with a smartphone application via Bluetooth, such that the voltage adjustment controls can be controlled by the smartphone application.

8. The vaporizer device of claim 1, wherein the single vaporizer housing comprises a respective plurality of vaporizer subcomponent housings attached together and each having a vaporizer cartridge opening and a battery device opening.

9. The vaporizer device of claim 1, wherein the single vaporizer housing includes a slider assembly configured to accept the plurality of vaporizer batteries having different vertical heights.

10. The vaporizer device of claim 4, wherein the single fire button is configured to pass voltage from the vaporizer batteries to the vaporizer cartridges such that the respective product in the respective vaporizer cartridges is vaporized simultaneously.

11. The vaporizer device of claim 5, wherein the respective plurality of fire buttons are configured to permit the respective product in the respective vaporizer cartridges to be vaporized independently.

12. The vaporizer device of claim 1, further comprising a riser configured for magnetic attachment to a side of the single vaporizer housing from which the vaporizer cartridges protrude.

13. The vaporizer device of claim 1, further comprising a single charging port configured to permit recharging of the plurality of vaporizer batteries.

* * * * *